United States Patent [19]
Cheng et al.

[11] Patent Number: 5,869,250
[45] Date of Patent: Feb. 9, 1999

[54] METHOD FOR THE IDENTIFICATION OF PEPTIDES THAT RECOGNIZE SPECIFIC DNA SEQUENCES

[75] Inventors: Xiaojun Cheng; R. L. Juliano, both of Chapel Hill, N.C.

[73] Assignee: The University of North Carolina at Chapel Hill, Chapel Hill, N.C.

[21] Appl. No.: 753,829

[22] Filed: Dec. 2, 1996

[51] Int. Cl.[6] ........................................ C12Q 1/68
[52] U.S. Cl. ........................................................ 435/6
[58] Field of Search ....................................... 435/6

[56] References Cited

PUBLICATIONS

J.J. Li et al., "Isolation of ORC6, a Component of the Yeast Origin Recognition Complex by a One–Hybrid System", Science 262: 1870–1874, Dec. 1993.

C. Inouye et al., "Isolation of a cDNA Encoding a Metal Response Elelment Binding Protein Using a Novel Expression Cloning Procedure: The One Hybrid System", DNA Cell Biol. 13(7): 731–742, Jul. 1994.

M. Yang et al., "Protein–Peptide Interactions Analyzed With the Yeast Two–Hybrid System", Nuc. Acids Res. 23(7): 1152–1156, Mar. 1995.

*Primary Examiner*—Rebecca E. Prouty
*Attorney, Agent, or Firm*—Myers Bigel Sibley & Sajovec

[57] ABSTRACT

A method for identifying biologically significant peptide-DNA binding interactions and sequence-specific DNA-binding peptides in vivo using combinatorial oligonucleotide libraries is disclosed. Target DNA sequences include promoter sequences, 5' and 3' regulatory sequences, and exon and intron regulatory sequences. Preferably, a yeast combinatorial library is employed. Peptides that bind to specific DNA sequences, identified by the above method, are disclosed. Also disclosed is a method for identifying non-toxic compounds that inhibit gene expression in host cells in vivo.

33 Claims, 8 Drawing Sheets

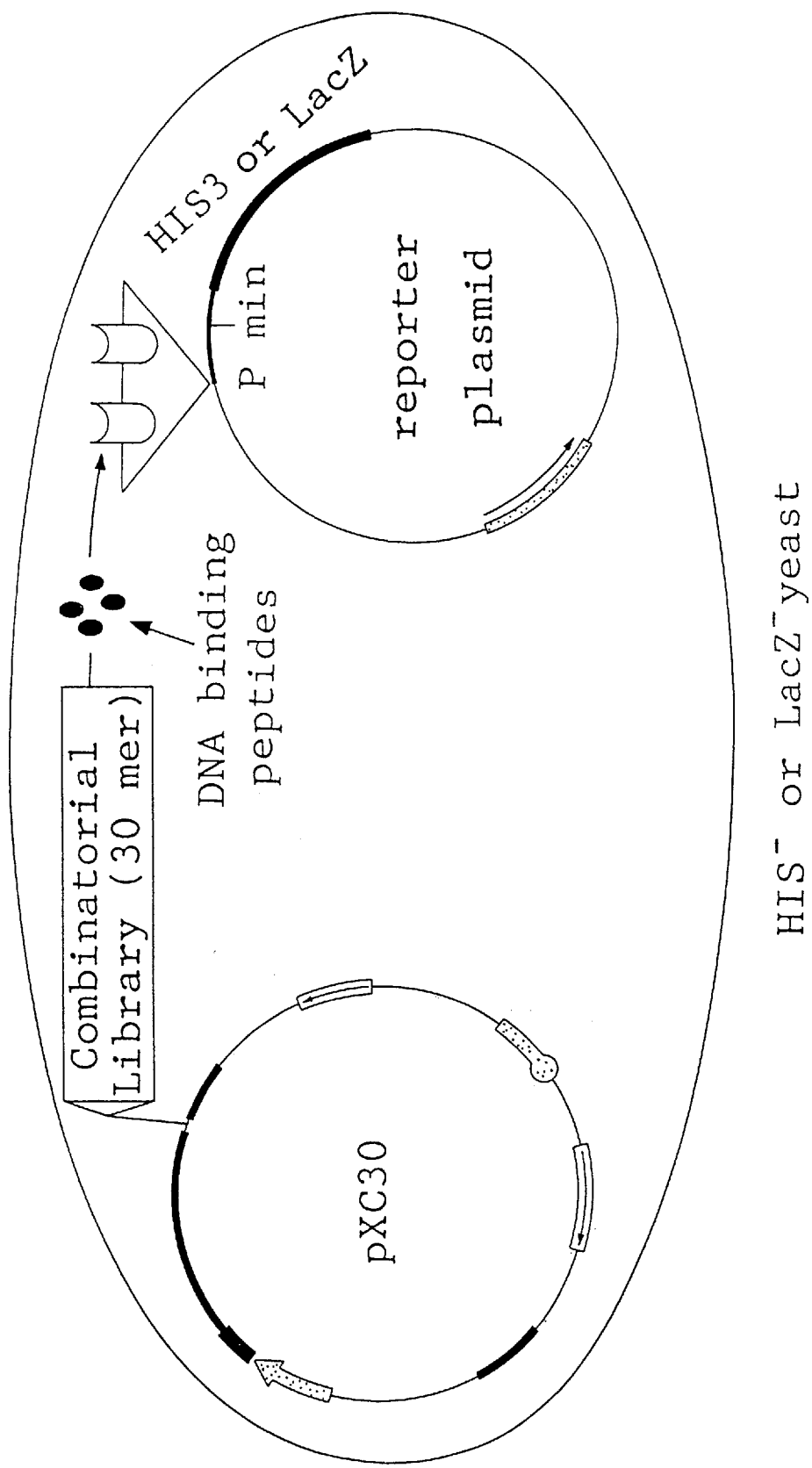
FIG. IC

FIG. 4

Sequence-Specific DNA Binding Peptides
(prefer wild-type binding sites):

| | | | | |
|---|---|---|---|---|
| A46-2 | (SEQ ID NO:5): | QGAISNGTGD | AGPGWLKRPP | FWNPERPNNK |
| G1-2 | (SEQ ID NO:6): | WQRMRVWDEC | GIMGSDHPLE | LNECPGEYTV |
| G12-1 | (SEQ ID NO:7): | AESKLMRGVI | LPLKSILYRL | RFRLRCYRLW |
| H3-2 | (SEQ ID NO:8): | NDRVFGDYSY | FGGACAFVLA | FGSVCCGELC |
| H9-1 | (SEQ ID NO:9): | WPVRRRNRNC | CVWDGGYWDF | CGADCDAVCV |
| H13-4 | (SEQ ID NO:10): | NVSVVCAVVW | FSCSLVSYAS | GVYGGGSDSG |
| K20-1 | (SEQ ID NO:11): | MRRLIYGHAP | LQNNALSCRQ | GAGPKGAERL |
| K38-2B | (SEQ ID NO:12): | EVWLYRGPLL | WSIAKKAFYA | VLMGMVVLVL |

Sequence-Specific DNA Binding Peptides
(prefer mutant binding sites):

| | | | | |
|---|---|---|---|---|
| G4-4 | (SEQ ID NO:13): | VFRPLTFEST | FFNSGLLFQT | GTTLNPISVY |

Non-Specific DNA Binding Peptides*:

| | | | | |
|---|---|---|---|---|
| A97-3 | (SEQ ID NO:14): | RRCAGLASRV | TSRSLGELEG | ANSLRKYFRR |
| H18-1 | (SEQ ID NO:14): | RRCAGLASRV | TSRSLGELEG | ANSLRKYFRR |

*These two non-specific DNA binding peptides (A97-3 and H18-1) have the same nucleotide sequence, and were identified in two different rounds of screening.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

G A G G C G T G G C     1 0

(2) INFORMATION FOR SEQ ID NO:2:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

AAAGCGTGGC                            10

(2) INFORMATION FOR SEQ ID NO:3:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

TTTCCAGGGA GGCG                    14

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

CGCCGGGGCG                            10

(2) INFORMATION FOR SEQ ID NO:5:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

Gln Gly Ala Ile Ser Asn Gly Thr Gly Asp Ala Gly Pro Gly Trp Leu
1               5                   10                  15

Lys Arg Pro Pro Phe Trp Asn Pro Glu Arg Pro Asn Asn Lys
            20                  25                  30

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:6:

Trp Gln Arg Met Arg Val Trp Asp Glu Cys Gly Ile Met Gly Ser Asp
1               5                   10                  15

```
          His  Pro  Leu  Glu  Leu  Asn  Glu  Cys  Pro  Gly  Glu  Tyr  Thr  Val
                    20                  25                       30
```

(2) INFORMATION FOR SEQ ID NO:7:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:7:

```
Ala  Glu  Ser  Lys  Leu  Met  Arg  Gly  Val  Ile  Leu  Pro  Leu  Lys  Ser  Ile
1               5                        10                       15

Leu  Tyr  Arg  Leu  Arg  Phe  Arg  Leu  Arg  Cys  Tyr  Arg  Leu  Trp
               20                       25                       30
```

(2) INFORMATION FOR SEQ ID NO:8:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:8:

```
Asn  Asp  Arg  Val  Phe  Gly  Asp  Tyr  Ser  Tyr  Phe  Gly  Gly  Ala  Cys  Ala
1               5                        10                       15

Phe  Val  Leu  Ala  Phe  Gly  Ser  Val  Cys  Cys  Gly  Glu  Leu  Cys
               20                       25                       30
```

(2) INFORMATION FOR SEQ ID NO:9:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:9:

```
Trp  Pro  Val  Arg  Arg  Arg  Asn  Arg  Asn  Cys  Cys  Val  Trp  Asp  Gly  Gly
1               5                        10                       15

Tyr  Trp  Asp  Phe  Cys  Gly  Ala  Asp  Cys  Asp  Ala  Val  Cys  Val
               20                       25                       30
```

(2) INFORMATION FOR SEQ ID NO:10:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:10:

```
Asn  Val  Ser  Val  Val  Cys  Ala  Val  Val  Trp  Phe  Ser  Cys  Ser  Leu  Val
1               5                        10                       15

Ser  Tyr  Ala  Ser  Gly  Val  Tyr  Gly  Gly  Gly  Ser  Asp  Ser  Gly
               20                       25                       30
```

( 2 ) INFORMATION FOR SEQ ID NO:11:

( i ) SEQUENCE CHARACTERISTICS:
        ( A ) LENGTH: 30 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:11:

```
Met Arg Arg Leu Ile Tyr Gly His Ala Pro Leu Gln Asn Asn Ala Leu
1               5                   10                  15
Ser Cys Arg Gln Gly Ala Gly Pro Lys Gly Ala Glu Arg Leu
                20                  25                  30
```

( 2 ) INFORMATION FOR SEQ ID NO:12:

( i ) SEQUENCE CHARACTERISTICS:
        ( A ) LENGTH: 30 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:12:

```
Glu Val Trp Leu Tyr Arg Gly Pro Leu Leu Trp Ser Ile Ala Lys Lys
1               5                   10                  15
Ala Phe Tyr Ala Val Leu Met Gly Met Val Val Leu Val Leu
                20                  25                  30
```

( 2 ) INFORMATION FOR SEQ ID NO:13:

( i ) SEQUENCE CHARACTERISTICS:
        ( A ) LENGTH: 30 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:13:

```
Val Phe Arg Pro Leu Thr Phe Glu Ser Thr Phe Phe Asn Ser Gly Leu
1               5                   10                  15
Leu Phe Gln Thr Gly Thr Thr Leu Asn Pro Ile Ser Val Tyr
                20                  25                  30
```

( 2 ) INFORMATION FOR SEQ ID NO:14:

( i ) SEQUENCE CHARACTERISTICS:
        ( A ) LENGTH: 30 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:14:

```
Arg Arg Cys Ala Gly Leu Ala Ser Arg Val Thr Ser Arg Ser Leu Gly
1               5                   10                  15
Glu Leu Glu Gly Ala Asn Ser Leu Arg Lys Tyr Phe Arg Arg
                20                  25                  30
```

METHOD FOR THE IDENTIFICATION OF PEPTIDES THAT RECOGNIZE SPECIFIC DNA SEQUENCES

This invention was made with Government support under Grant Number CA47044 from the National Institute of Health. The Government has certain rights to this invention.

FIELD OF THE INVENTION

This invention relates to a strategy for the identification and characterization of peptides that recognize specific DNA sequences by use of combinatorial oligonucleotide libraries.

BACKGROUND OF THE INVENTION

Previous investigations have been directed at developing methods for identifying specific peptide-peptide or peptide-nucleotide interactions.

U.S. Pat. No. 5,498,530 to Schatz and U.S. Pat. No. 5,270,170 to Schatz describe a method for isolating novel peptide ligands that bind to receptor molecules of interest using phage display combinatorial library techniques. The '530 patent concerns the method of constructing the combinatorial peptide library used in the '170 patent. The methods described involve the use of combinatorial libraries to express fusion proteins, but employ in vitro binding affinity. These references involve neither a reporter plasmid having a reporter gene driven by a target DNA sequence nor a transactivating domain of a transcription factor in the fusion protein. They do not teach identification of peptides by functional expression and selection.

Rebar and Pabo, *Science* 263, 671–673 (1994) discloses a method for identifying peptides that have high affinity to specific nucleotide sequences, specifically zinc finger binding sequences, using phage display combinatorial library techniques and affinity selection. Like Schatz, the method disclosed here, while employing fusion protein expression and random oligonucleotides cloned into a DNA vector, does not involve a functional expression selection strategy.

PCT Application WO 96/06166 to Choo et al., and Choo et al., *Nature* 372, 642–645 (1994), disclose a method for identifying zinc-finger DNA-binding proteins using phage display combinatorial library techniques and affinity selection in combination with rational design. In addition to the method of identification, the patent also describes a method of using the selected DNA-binding peptide to block/alter gene expression in mammalian cells. However, neither the paper nor the patent application discloses selection of DNA-binding peptides or drugs by functional expression.

U.S. Pat. No. 5,498,538 to Kay and Fowlkes describes a method for identifying a protein, polypeptide or peptide which binds to a ligand of choice by screening a library of recombinant vectors in which each vector expresses a fusion protein containing a binding domain and an effector domain that enhances expression or detection of the binding domain. The specification discloses only affinity selection using magnetic beads in vitro. Functional selection in vivo by activating the expression of a reporter gene in a reporter plasmid is not contemplated, and screening based on the death or survival of transformed cells is not envisioned.

The foregoing all fail to provide a method of identifying biologically significant peptide-DNA binding events. Accordingly, there is an ongoing need for improved methods of identifying and characterizing peptide-DNA interactions.

SUMMARY OF THE INVENTION

Disclosed herein is a unique strategy for identifying biologically significant peptide-DNA binding interactions.

A first aspect of the present invention is a method for identifying sequence-specific DNA-binding peptides, comprising the steps of: (a) providing host cells containing selectable markers; (b) providing a recombinant vector containing a coding sequence encoding a protein that activates gene expression when in proximity to a target DNA sequence, the DNA sequence comprising a regulatory element, and the recombinant vector containing a selectable marker; (c) inserting into the coding sequence in a plurality of recombinant vectors a random oligonucleotide so that the resulting vectors encode a plurality of different fusion proteins, each containing the protein of step (b) and a peptide encoded by the random oligonucleotide; (d) providing a reporter vector, the reporter vector comprising a reporter gene, the DNA regulatory element of step (b), and a selectable marker; (e) co-transfecting the host cells with the DNA vectors of step (c) and the reporter vectors, and then (f) culturing the transfected host cells in a selective medium, so that only those host cells containing a vector DNA of step (c) expressing a fusion protein that contains a peptide capable of sequence-specific binding to the target DNA sequence of step (d) grow therein.

A second aspect of the present invention is peptides that have been identified by the above method.

A third aspect of the present invention is a method of identifying a compound that inhibits gene expression. The method comprises a) providing an expression vector that expresses a transcriptional factor; b) providing a reporter plasmid containing a gene encoding an enzyme (e.g., thymidine kinase) and a target DNA sequence of said transcriptional factor located 5' to said gene; c) co-transfecting host cells with said expression vector and said reporter plasmid, said transcriptional factor binding specifically to said target DNA sequence and activating said enzyme expression; d) administering a pro-toxin (e.g., ganciclovir) to said transfected cells, said pro-toxin being converted by said enzyme to a product that is lethal to said cells; e) administering a test compound to said transfected cells, whereby a compound capable of inhibiting the expression of said enzyme are identified by the survival of said cells.

The foregoing and other objects and aspects of the present invention are explained in detail in the drawings herein and the specification set forth below.

BRIEF DESCRIPTION OF THE DRAWINGS

FIGS. 1A–C illustrates the process of identifying sequence-specific DNA-binding peptides using the present invention.

FIG. 1A: Construction of HIS3 or LacZ reporter plasmids.

FIG. 1B: Construction of the yeast 30 mer combinatorial library (pXC30).

FIG. 1C: HIS– or LacZ– yeast strains were transformed with the appropriate reporter plasmid. Transformed yeast cells were then transformed with pXC30. Clones displaying HIS+ or LacZ+ phenotypes were identified, and the combinatorial library insert was isolated and sequenced.

FIG. 2A: Construction of the yeast activation vector (pXC). The procedures for the construction of the pXC vector were as follows: (1) Restriction of the Kpn I-BamH I fragment from pPC62 and ligation of this fragment into pRS313 or pRS314, which contain TRP1 or LEU2 markers respectively. (2) The BamH I site of the above vectors was destroyed by cutting with BamH I, blunting, and religating the vectors. (3) DNA encoding the partial N-terminus of the transcription factor Sp1 was amplified by polymerase chain reaction, followed by in-frame ligation into the above vectors at Sal I and Cla I sites. (4) The vectors were then restricted with BamH I and Spe I. There is no BamH I site in the Sp1 fragment. (5) An oligonucleotide was synthesized which contained a flexible linker encoding ten amino acids and multiple cloning sites, including Bgl II, Cla I, EcoR I, Sma I, BamH I, Nsi I, and Spe I. (6) Double-stranded oligonucleotide was made using DNA polymerase. (7) The double-stranded oligonucleotide was restricted with Bgl II and Spe I. (8) The restricted oligonucleotide was ligated into the compatible BamH I and Spe I sites of the vectors. The BamH I site in the Sp1 fragment is now destroyed by the ligation.

FIG. 2B: Construction of the vector for the yeast combinatorial library (pXCLF2). This vector was constructed by first inserting a partial binding domain (two zinc fingers) of Sp1 into pXC at EcoR I and BamH I sites. The yeast combinatorial library pXC30 was constructed by ligating a 90 mer synthetic oligonucleotide library (encoding a 30 mer peptide library) downstream from the partial DNA binding domain in pXCLF2.

FIG. 2C: Construction of the pXCF3 vector. Three zinc fingers of Sp1 were inserted into the pXC vector at EcoR I sites and BAMH I sites.

FIG. 4 presents the putative sequences of peptides expressed in the combinatorial library that exhibited sequence-specific or non-specific binding to wild-type (SEQ ID NO:1) and mutant (SEQ ID NO:2) Sp1 DNA binding sites.

DETAILED DESCRIPTION OF THE INVENTION

Figure 1A:
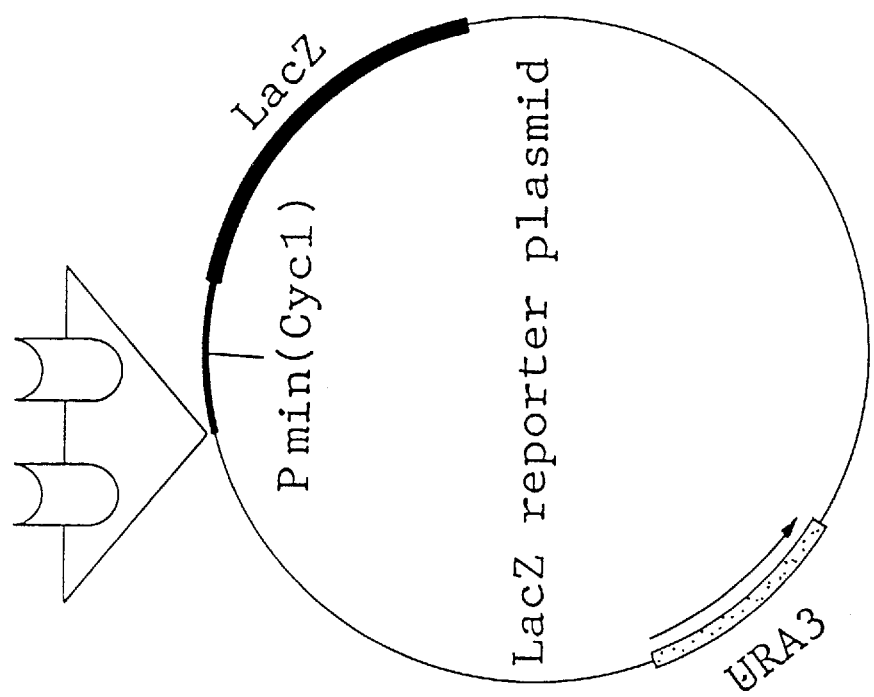

Amino acid sequences disclosed herein are presented in the amino to carboxyl direction, from left to right. The amino and carboxyl groups are not presented in the sequence. Nucleotide sequences are presented herein by single strand only in the 5' to 3' direction, from left to right. Nucleotides and amino acids are represented herein in the manner recommended by the IUPAC-IUB Biochemical Nomenclature Commission, or (for amino acids) by either one letter or three letter code, in accordance with 37 CFR § 1.822 and established usage. Where one letter amino acid code is used, the same sequence is also presented elsewhere in three letter code.

In overview, the present invention involves the use of combinatorial peptide libraries to identify peptides that bind to DNA in a sequence-specific manner. The present invention can be used to identify peptides that bind to any target DNA sequence and thereby modify gene expression. Preferably, the invention is directed toward identifying peptides that target promoter sequences, 5' regulatory sequences, 3' regulatory sequences, or exon and intron regulatory sequences, more preferably promoter sequences.

There are two distinct aspects to the present invention. The first concerns a method for the selection of factors that bind at specific DNA sequence and activate gene expression (see FIG. 1). The second aspect relates to a method for the selection of compounds that specifically block a transcriptional event (see FIG. 3).

Identifying Peptides that Activate Gene Expression.

Several approaches have previously been used to provide selective control of gene expression. The delivery and expression of exogenous genes ("gene therapy"), or use of homologous recombination ("knock outs"), provide permanent changes in gene expression. More pharmacological techniques have been used to transiently modulate expression of specific genes using anti-sense oligonucleotides or ribozymes directed against the mRNA of the targeted gene.

A powerful approach for identification of peptides capable of recognizing specific target DNA sequences involves the use of combinatorial libraries. These methods entail the random generation of very large numbers of molecules, followed by the selection of those few molecules that recognize the specific target. One particular technique is the use of phage display libraries where DNA inserts coding for random peptide sequences are fused to a coat protein gene of a filamentous phage. Peptides with affinity for a particular ligand, expressed on the phage surface can be identified by selecting phage capable of binding to the immobilized ligand. Disclosed herein is a strategy for the identification of selective DNA-binding peptides that is much more rapid and powerful than phage display. This strategy involves the use of combinatorial peptide libraries containing completely random peptides. Such peptides can potentially block initiation of transcription if targeted to 5' regulatory regions of genes, or block transcriptional processing if targeted to exon or intron sequences.

There are three steps to practicing this method, as demonstrated by the following illustrative embodiment:

1) Construction of a combinatorial library. To express in yeast a large number of peptides from which desired peptides are selected, a vector was constructed that expresses part of the yeast transcription factor Gal4. The transactivation domain of Gal4 activates gene transcription. There is a polylinker at the 3'end of the coding region of the Gal4 gene in the vector. A library is constructed by inserting in-frame oligonucleotide randomers at the polylinker of the vector. Thus, the library expresses, when transformed into yeast cells, a large number of fusion proteins. Each fusion protein contains the transactivation domain of Gal4 at the N-terminus and a peptide encoded by a randomer oligonucleotide. In addition, the library vector also contains the selectable marker TRP1.

2) Construction of reporter plasmid. The reporter plasmid contains a reporter gene, such as the HIS3 gene. The target DNA sequence to which the desired peptide binds is inserted 5' to the minimal promoter driving the HIS3 gene. In addition, the plasmid also contains a selectable LEU2 marker.

3) Transformation and selection. A yeast host strain is selected that is HIS–, LEU–, and TRP–. Thus, when the host cells are co-transformed with the combinatorial libraries and the reporter plasmids, only those yeast cells that contain both of the reporter plasmids and a library vector that expresses a peptide with binding specificity to the target DNA sequence in the reporter plasmid would survive in HIS, LEU, and TRP deficient culture media. This is because when a library peptide binds to the target DNA sequence, the Gal4 transactivating domain linked to the peptide activates the transcription of the HIS3 gene. The yeast cells obtained can be cultured and the vector DNA can be isolated for analysis of the oligonucleotide sequence that encodes for the selected peptide.

In one embodiment of the present invention the transactivation domain of the fusion protein is derived from the yeast Gal4 protein. It will be appreciated by those skilled in the art that any transactivation domain, for example the transactivation domain of the yeast GCN4 or ADR1 proteins, can be used to carry out the present invention.

The embodiment illustrated above identifies peptides that exhibit sequence-specific binding to the DNA binding site for the transcription factor Sp1. It will be understood by those skilled in the art that the present invention can be used to identify peptides that bind to any target DNA site so as to modify gene expression. Preferable target DNA sequences include promoter sequences, 5' and 3' regulatory sequences, or exon and intron regulatory sequences, more preferably promoter sequences.

Likewise, in the illustrative embodiment above, the fusion protein contained an incomplete Sp1 DNA binding domain. The present invention was used to identify peptides within the combinatorial library that could reconstitute the DNA binding activity of the truncated Sp1 DNA binding domain. In alternate embodiments, the invention can be employed with other truncated DNA binding domains, including those not based on a zinc finger motif. As a further alternative, the present invention can be carried out in the absence of any fixed partial DNA binding domain. In other words, the entire DNA binding domain of the fusion protein may be encoded by the degenerate peptide from the combinatorial library.

In one embodiment of the invention using the mammalian Sp1 transcription factor, a spacer may be necessary between the Gal4 transactivating domain and the DNA binding domain fused to the Gal4 domain to achieve high level transcriptional activation of the reporter gene.

"Sequence-specific" binding, as used herein, can be assessed by functional means. Sequence-specific binding by the fusion protein to the target DNA is binding of a sufficient affinity to trigger or block a biological function, i.e., gene transcription. Alternatively, sequence-specific binding can be assessed by measuring the binding affinity of the fusion protein to the target DNA. There is no particular upper or lower limits for the dissociation constants for fusion protein binding to target DNA as carried out by the instant invention. Dissociation constants for fusion protein-target DNA binding can be as high as $10^{-9}$, $10^{-10}$, or $10^{-11}$ moles/liter or higher. Likewise, dissociation constants for fusion protein-target DNA binding can be as low as $10^{-8}$, $10^{-7}$, $10^{-6}$ moles/liter.

Identifying Peptides that Block Gene Expression.

The second aspect of the invention is a strategy to rapidly screen for compounds that interfere with transcriptional activation by specific transcription factors using an expression system. The compound can block transcription by interacting with the transcription factor itself or with a DNA sequence recognized by the transcription factor (see FIG. 3). Alternately, the compound can be a protein to which the transcription factor normally binds, either on or off the DNA, thereby preventing the transcription factor from binding thereto and interfering with transcription. Such protein binding partners may be transcription factors themselves. The embodiments of the invention described above may or may not employ combinatorial libraries.

In one illustrative embodiment of the invention, yeast cells are co-transfected with both a vector expressing a mammalian transcription factor and a vector containing the gene for herpes virus thymidine kinase (TK) driven by a promoter sequence that is recognized by the transcription factor. Thus, normally the transfected yeast cells express TK. When ganciclovir is added to the medium and is taken up by the yeast cells, the TK phosphorylates the ganciclovir and makes it lethal to the cells, leading to cell death. When a second compound is added that prevents the transcription of the TK gene, however, the yeast cells survive. The compound may block transcription of the TK gene by binding to the target DNA site and preventing transcription factor binding thereto, or by binding to a second protein with which the transcription factor normally interacts. Alternately, the compound may interfere with transcription by binding directly to the transcription factor.

As used herein, a "pro-toxin" is a substance that is normally not harmful or toxic to the host cell, but it is converted into a toxic substance when acted upon by another agent. In a preferred embodiment of the present invention, ganciclovir is used as the pro-toxin and mammalian thymidine kinase is the agent that converts ganciclovir to a toxic form. One skilled in the art will appreciate that other enzyme/protoxin systems can be used in carrying out the present invention.

A "compound" as used herein is intended to be construed broadly and includes, but is not limited to, any naturally-occurring or synthetic element, chemical group or molecule. Organic compounds (i.e., those containing at least one carbon) are preferred (e.g., amino acids, peptides, proteins, nucleic acids, carbohydrates, alcohols, aldehydes, ketones, acids, amides, amines, esters, thiols, ethers, lipids, heterocyclic ring systems, and adenine derivatives (e.g., ATP, uric acid, coenzymes)).

In one embodiment of the invention the compound is simply added to the medium in which the host cells are cultured. Alternatively, the compounds to be screened may be expressed by a combinatorial library co-transfected into the host cells.

Methods of administering compounds to host cells include any method of adding a compound to the host cell medium in which the cells are contained. Compounds may be added to the cell medium in any form that facilitates their uptake by the cell, e.g., packaged in liposomes or delivered in the presence of dimethyl sulfoxide (DMSO).

Genetic Engineering Techniques.

The production and use of cloned genes, recombinant DNA, vectors, transformed host cells, selectable markers, proteins, and protein fragments by genetic engineering are well-known to those skilled in the art. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col 3 line 26 to Col 14 line 12; and U.S. Pat. No. 4,879,224 to Wallner at Col. 6 line 8 to Col. 8 line 59. All United States patent references cited herein are intended to be incorporated in their entirety by reference.

A "promoter sequence of a gene," as used herein, is a DNA sequence found upstream of a gene that acts as a signal for the binding of RNA polymerase, which leads to transcriptional activation.

A "minimal promoter" is a part of a promoter sequence that is necessary, but not sufficient, to drive transcription. The minimal promoter contains sequences that are necessary for the basal transcription apparatus, including the RNA polymerase, to bind.

A vector is a replicable DNA construct. Vectors are used herein to amplify DNA encoding the fusion proteins or reporter genes and to express the fusion proteins or reporter gene products of the present invention.

An expression vector is a replicable DNA construct in which a DNA sequence encoding a protein is operably linked to suitable control sequences capable of effecting the expression of proteins. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Suitable control sequences may vary according to the function of the particular expression vector. For some purposes it is advantageous to have an expression vector with a constitutive promoter recognized by the host cell. In other instances, it is more to have an expression vector with an inducible promoter or a promoter that is not recognized by the host cell that must be activated by exogenously provided transcription factors. With reference to the present invention, the expression of the combinatorial library is driven by a promoter that is recognized by the host cell. Likewise, in embodiments in which the invention is used to screen for compounds that inhibit transcription, the vector expressing the transcription factor contains a promoter recognized by the host cell. In contrast, as described below, the reporter vectors should contain promoters that are not recognized by the host cell and require exogenous factors for activation.

Amplification vectors do not require expression control domains. All that is needed is the ability to replicate in a host, usually conferred by an origin of replication, and a selection gene to facilitate recognition of transformants.

Reporter vectors comprise a sub-class of expression vectors. Reporter vectors are used herein to introduce a reporter gene into the host cell. The protein encoded by the reporter gene should not normally be present in the host cell. Expression of a reporter gene confers an easily-detectable phenotype on the host cell.

In carrying out the present invention, the reporter gene should carry a promoter that is not recognized by the host organism. When using the invention to identify peptides that activate transcription, the reporter gene is activated by an exogenous transcription-activating protein in the combinatorial library. In this manner, expression of the reporter gene is a positive indicator that the host cell contains a library sequence which expresses a peptide that binds to the target DNA. When the invention is used to identify compounds that inhibit transcription, the promoter driving TK expression should recognize the transcription factor under investigation.

Reporter genes compatible with various host cell systems are known. Reporter genes useful in yeast cells include those containing the HIS3, LEU2, or TRP1 genes. These reporter vectors are used in conjunction with host yeast strains that are deficient in endogenous HIS3, LEU2, or TRP1 function, respectively. In a preferred embodiment of the invention, the herpes viral thymidine kinase gene is employed as a reporter in yeast cells. In higher eukaryote host cells the *E. coli* chloramphenicol acetyltransferase (CAT) and firefly luciferase genes are examples of commonly-used reporter genes. There is little or no background activity for these enzymes in the commonly-employed higher eukaryotic host cell systems. More recently, the green fluorescent protein (GFP) of the jellyfish Aequorea Victoria has been used as a reporter gene in a wide variety of microbial, plant, insect and mammalian cells. GFP is a species-independent reporter that requires no substrate in order to fluoresce. A. Crameri et al., *Nature Biotech.* 14, 315–319 (1996). Other reporter gene systems compatible with these and other host cell systems are well known to those skilled in the art.

Vector DNA generally replicates and functions independently of the host genome, but may, in some instances, integrate into the genome itself. Suitable vectors for practicing the present invention include plasmids, viruses (e.g., adenovirus, cytomegalovirus), phage, retrovirus and integrated DNA fragments (i.e., fragments integratable into the host genome by recombination). In a preferred embodiment of the invention, plasmid vectors are used to transform host cells.

Suitable host cells include prokaryotes, lower eukaryotes (i.e., yeast), or cells from higher eukaryotic organisms. In a preferred embodiment of the invention yeast are employed as host cells. Culturing of host cells may be carried out by any suitable technique. Prokaryote host cells include gram negative or gram positive organisms, for example *Escherichia coli* (*E. coli*) or Bacilli. Higher eukaryotic cells include established cell lines of mammalian origin as described below.

Transformed host cells are cells which have been transformed or transfected with vectors containing DNA coding for fusion proteins or carrying the reporter gene used to practice the method of the present invention. Transformed host cells ordinarily express protein, but host cells transformed for purposes of cloning or amplifying DNA coding for the proteins of the present invention need not express protein.

The term "co-transfection" as used herein indicates transfection of host cells with more than one vector, such that the host cell contains at least one copy of each of the transfected vectors. Said multiple transfections need not be carried out simultaneously, however, but may instead be performed sequentially over time. Transfection may be carried out by any suitable means, such as methods employing liposomes, microinjection, cell fusion, DEAE-dextran, calcium phosphate precipitation, electroporation, microparticle bombardment, conjugation into a complex internalized into a cell (see, e.g., D. Curiel et al., U.S. Pat. No. 5,521,291), and other techniques known to those skilled in the art.

A broad variety of suitable prokaryotic and microbial vectors are available. See Maniatis et al., MOLECULAR CLONING, Cold Spring Harbor Laboratory (1982). pBR322 or a plasmid derived therefrom is often used to transform *E. coli*. See Bolivar et al., *Gene* 2, 95 (1977). Promoters commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc Natl. Acad. Sci. USA* 80, 21 (1983)). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980)).

Eukaryotic microbes such as yeast may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977)). The presence of the trp1 lesion in the yeast host cell genome then provides an effective environment for detecting transformation by growth in the absence of tryptophan.

Suitable promoting sequences in yeast vectors include the promoters for metallothionein, alcohol dehydrogenase, adenylate cyclase, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells. Generally, identification is by survival of transformants in culture medium that is toxic, or from which the cells cannot obtain critical nutrition without having taken up the marker protein.

The previous discussion concerns selection of suitable vectors and control sequences for different host cell systems. As described previously, in some instances desirable control sequences will be recognized by the host cell. In contrast, in carrying out the present invention, transcription of the reporter genes is driven by promoter sequences not recognized by the host cell. The promoters selected to drive transcription of the reporter genes should be activated only by exogenous transcription factors.

A "coding sequence," as used herein, is a nucleotide sequence that can be translated into the amino acid sequence of a peptide or protein chain. A coding sequence encodes the structure of a peptide or protein rather than containing functional regions, such as promoter or enhancer regions or signals relating to transcription initiation or termination, for example.

An intron is a DNA sequence found within most eukaryotic genes, which interrupts the code for the gene product. Introns are also sometimes referred to as intervening sequences. The full DNA sequence is initially transcribed as heterogeneous nuclear RNA (hnRNA), and then the intron sequences are removed to give the final mRNA molecule.

Exons are the protein-encoding parts of the gene. The exons encode the final mRNA. In most eukaryotic genes, the exons are separated by non-coding intron sequences. The final mRNA is produced after the introns are spliced out of the hnRNA molecule.

Gene Expression.

Gene expression as used herein encompasses all steps in the synthesis of a functional peptide or protein from DNA. There is evidence that gene expression can be controlled at each of these steps: at the transcriptional, post-transcriptional, translational, and post-translational levels. B. Alberts et al., MOLECULAR BIOLOGY OF THE CELL, 2d edition, Garland Publishing, Inc. (1989), p. 553. Transcriptional regulation includes initiation of transcription, enhancement of the level of transcription, and altering transcription start and stop site selection. Examples of points at which post-transcriptional control of gene expression may be exerted include: the rate of RNA turnover, mRNA export from eukaryotic nuclei, RNA splicing or processing, and attachment of mRNA to ribosomes for translation. Post-translational processing steps include peptide/protein modifications, such as methylation or phosphorylation, peptide/protein folding and cross-linking to produce secondary or tertiary structures, and peptide/protein aggregation to form quaternary structures. Post-translational regulation of gene expression can also be effected by increasing or decreasing peptide/protein stability and turnover rates.

The present invention can be used to identify peptides that interact with DNA so as to regulate gene expression at the transcriptional level. Peptides may activate transcription by binding at promoter sequences. Alternately, they may activate or enhance the rate of transcription by binding at 5' or 3' regulatory sequences. As a further alternative, peptides may regulate transcription by interacting with regulatory sequences within exons or introns. It will be appreciated by those skilled in the art that the peptides of the present invention can bind directly to the DNA or they may bind to other protein or peptide factors that bind to the DNA.

Transcription Factors and Transcriptional Activation.

As used herein, a "protein that controls gene transcription" is a protein that regulates or modulates gene expression at the transcriptional level by binding at its target DNA site. Binding may be to the target DNA itself or to other peptide or protein factors that bind to the target DNA site. Such control or regulation includes, but is not limited to, activating the initiation of transcription, enhancing the level of transcription, and altering transcription start and stop site selection. Some forms of transcriptional control involve activation or upregulation, others concern alterations or modulations in the pattern of expression. Proteins that alter expression patterns may have either activation or suppressor function, or both.

A DNA "regulatory element" is any DNA sequence that regulates gene expression at the transcriptional level, as described above. Preferred DNA regulatory elements include promoter sequences, 5' and 3' regulatory sequences, and regulatory sequences within exons and introns, more preferably promoter sequences. Exemplary DNA regulatory elements include, but are not limited to, DNA sequences that control the initiation of transcription, the level of transcription, and transcription start and stop site selection.

The phrase "protein that controls gene transcription when in proximity" to a DNA regulatory element signifies a fusion protein of the present invention, containing a library peptide, that specifically binds at a target DNA sequence so as to control or regulate gene transcription. By proximity, it is meant close enough to effect changes in transcription of the reporter gene. Alternatively, proximity means binding to the target DNA sequence itself or to other peptide or protein factors that bind to the target DNA sequence. Such peptide or protein factors may also be transcription factors.

A "target DNA sequence" of a protein or transcription factor is the DNA sequence at which the protein/transcription factor binds so as to modulate gene transcription. The protein/transcription factor may bind directly to the target DNA or to other proteins that bind to the target DNA site. Such proteins may also be transcription factors.

A protein that activates gene transcription is broadly construed herein to include fusion proteins, containing library peptides, that are required either to initiate or to enhance the level of gene transcription, or both. These proteins are commonly referred to as transcription factors by those skilled in the art. Transcription factors can come from any host source, prokaryotic or eukaryotic. "Protein" can indicate, in some embodiments of the invention, only a portion of an intact protein. In a preferred embodiment of the present invention, for example, only the transactivational domain of the yeast Gal4 transcription factor is used to carry out the claimed method.

As used in reference to the present invention, a protein that activates gene transcription when in proximity to a promoter sequence of a gene indicates a protein that is close enough to activate transcription of the reporter gene. Stated otherwise, by proximity it is meant close enough to achieve physical contact with the RNA polymerase itself or other proteins in the transcriptional apparatus or other transcription factors that bind at or near the promoter sequence. It will be understood by those skilled in the art that protein dimensions vary greatly. In addition, it is well-known that the transcriptional apparatus may involve multiple proteins. Thus, there is no upper or lower limit to the distance between the target DNA site and the transcription start site of the reporter gene, with distances of 50, 100, 200, 500, 1000, 2000 or more nucleotides being suitable.

Combinatorial Libraries.

As used herein, "combinatorial library" refers to collections of diverse oligomeric biomolecules of differing sequence, which can be screened simultaneously for binding activity to a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic. Techniques for constructing combinatorial libraries of oligomeric biomolecules to identify those that specifically bind to a given target molecule are known.

In the case of a combinatorial peptide library, the peptides consist of sequences of the 20 naturally-occurring amino acids. Additional diversity is introduced into the population of peptides expressed by the combinatorial libraries as a result of post-translational modifications such as phosphorylation, amidation, or methylation. The peptides may be linear or may possess some form of higher order structure, such as disulfide cross-linking, alpha-helices, or beta-pleated sheets.

Peptides identified by practice of the present invention may be of any length. There is no particular upper limit on the length of the identified peptides, with peptides of 15, 30, 60 or 100 or more amino acids being suitable. There is also no particular lower limit on the length of the peptides identified by the present invention, with peptides of 60, 30, 15, 6 or fewer amino acids being suitable.

The nucleotide sequences which make up the peptide library form a pool of random oligonucleotides. In general, pools of random oligonucleotides comprise a plurality of distinct nucleic acid species in an aqueous solution. Each nucleic acid species in the pool includes a degenerate segment of nucleotides, in which each degenerate nucleotide position is randomly assigned both with respect to the other nucleotides in that segment of that species and with respect to nucleotides occupying the same position in other species in the degenerate pool. Note that "random" as used herein does not mean perfectly random: it merely means sufficiently random to provide a plurality of distinct species in the degenerate pool from which a particular species may be retrieved. Finally, each species in the degenerate pool may include non-random segments, such as primer segments or replication origins for amplification of the pool, though these segments may ultimately be removed from the final selected species.

Typically, from 16 to $10^{10}$ distinct nucleic acid species are included in the oligonucleotide pool, depending on the number of nucleotides being randomized. The precise number is not critical, though it is preferred that the number be sufficiently high to approach complete representation of all the possible members of the randomly represented set. There is no particular upper limit on the length of the nucleic acid species, with nucleic acids of 50, 100, 200 or 300 or more nucleotides being suitable. Likewise, there is no particular lower limit on the length of the nucleic acid species, with nucleic acids of 200, 100, 50, 20 or fewer nucleotides being suitable. The nucleic acid species may be linear or may possess some form of secondary structure, such as a stem and loop structure.

Peptides in the degenerate combinatorial library are expressed as part of a fusion protein. A fusion protein is a protein that is composed of regions derived from more than one parent peptide or protein. As practiced by the instant invention, a fusion protein is expressed from a fusion gene which is created by recombining the nucleotide sequence encoding one protein or peptide, or portion thereof, with the nucleotide sequence encoding at least one other protein or peptide, or portion thereof. In a preferred embodiment of the present invention, the fusion proteins are composed of the transactivation domain of a transcription factor fused to a peptide from the degenerate peptide library.

Uses of the Present Invention.

The method of the present invention is useful for identifying peptides that bind to specific DNA sequences. Advantages of the present method over those in the prior art include: (1) the present method is carried out in vivo and utilizes a functional screening method; thus, it identifies biologically-significant peptides; (2) the present method uses a combinatorial library approach, which generates a more diverse set of peptides than the natural cDNA libraries which have been utilized in previous investigations.

Another use of the peptides identified by the instant invention is as therapeutic "anti-gene peptides," which inhibit expression of cancer-associated genes by binding to target DNA sites and blocking binding and transcriptional activation by endogenous factors. Alternatively, fusion proteins containing binding domains identified by the present invention can be used to activate tumor suppressors or other "healthy" genes in tumor cells.

In addition, the present invention can be used to identify binding pairs, similar to the biotin-avidin binding pair system, which can be used as reagents in laboratory techniques such as sandwich assays.

The present invention is also useful in identifying compounds that inhibit gene expression in vivo by interfering with transcription factors. The compound may inhibit transcription factor activity by altering the structure or stability of the transcription factor or by binding to and blocking the transcription factor's DNA binding site. Compounds identified in this manner may also be useful as anti-cancer agents.

This particular embodiment provides a novel and advantageous method for screening compounds. This strategy has several advantageous features: (a) it is easily adapted to a 96-well format and is thus suitable for rapid screening by robotics; (b) the rapid growth of yeast cells contributes to the ease and rapidity of screening; and (c) since it utilizes is a positive selection for growth, candidate compounds that are themselves highly cytotoxic are automatically excluded.

Alternately, the present invention is useful as a control for industrial fermentation processes or other in vitro procedures. In this embodiment of the invention, cellular processes in cells grown in vitro can be controlled or "switched" on or off by the use of exogenous compounds. Thus in an industrial fermentation, for example, once cells reach a desired density, cell division can be switched off by the addition of an appropriate compound which interferes with the expression of genes promoting cell division.

The following examples are provided to illustrate the present invention, and should not be construed as limiting thereof.

EXAMPLE 1

Materials and Methods pRS313 and pRS314 vectors were purchased from ATCC. pPC62 and pRS315HIS vectors were kindly provided by Dr. R. Reed. p607Z vector was provided by Dr. B. West. yWAMz yeast strain was kindly provided by Dr. P. Hieter. yM4271 yeast strain was purchased from CLONTECH. Sp1 transcription factor cDNA was kindly provided by Dr. R. Tijian. A 100-base degenerate oligonucleotide was synthesized by Oligos Etc. All restriction enzymes were purchased from Boehringer Mannheim Corporation. Sequenase was purchased from USB.

EXAMPLE 2

Construction of the Vectors for Yeast Combinatorial Libraries

Figure 1A:
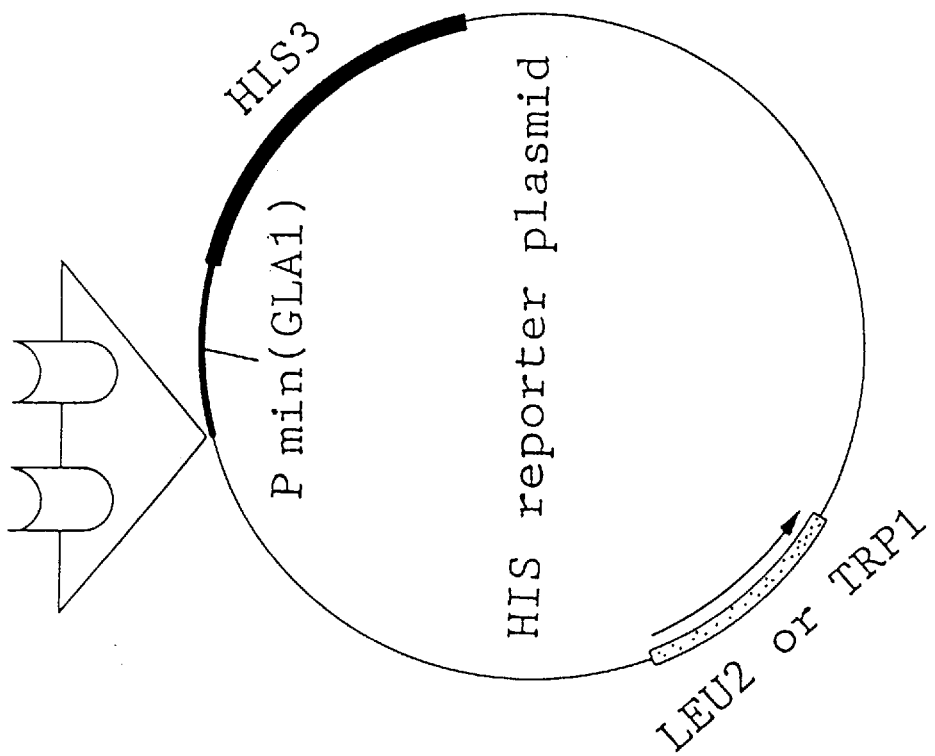
Figure 1B:
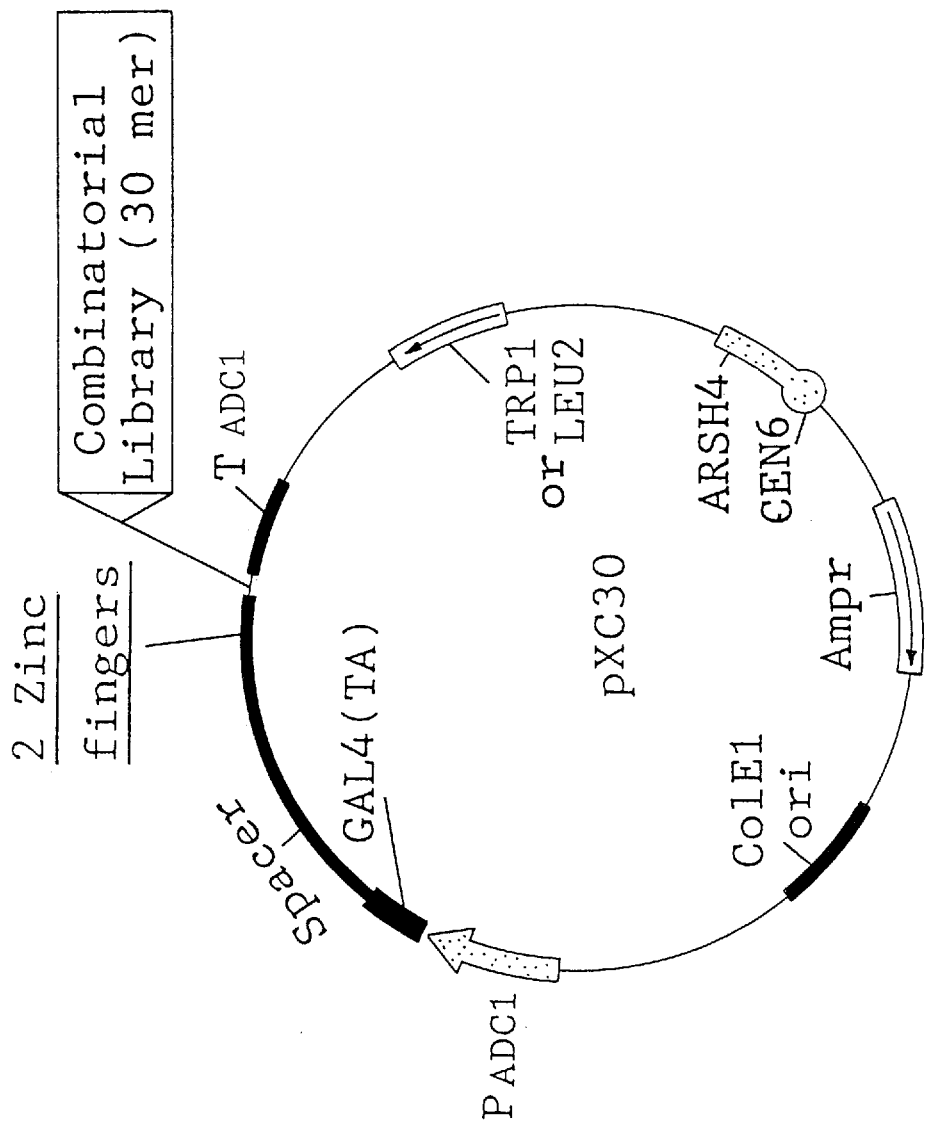

The vectors constructed for use in creating yeast combinatorial libraries are shown in FIG. 1. The essential structure of the yeast combinatorial libraries consists of three parts: the GAL4 activation domain, a partial DNA binding domain (two zinc fingers), and a synthetic oligo library. If binding vectors, such as pHR307a, pRS315HIS or pLG607Z, are used for inserting target sequences, a spacer between the GAL4 and the partial DNA binding domain may be necessary for the activation domain to interact with the transcription machinery.

The procedures for constructing the yeast combinatorial library vectors are briefly described as follows:

Step 1. Restriction of the Kpn I-BamH I fragment from pPC62 and ligation of this fragment into pRS313 and pRS314, which contain TRP1 or LEU2 markers respectively.

Step 2. Destruction of the BamH I sites of the above vectors by cutting with BamH I, blunting, and religating the vectors.

Step 3. Amplification by polymerase chain reaction of a DNA sequence encoding the partial N-terminus of transcription factor Sp1, and in-frame ligation of this fragment into the vectors at Sal I and Cla I sites.

Step 4. Restriction of the vectors with BamH I and Spe I. There is a BamH I site in the Sp1 fragment.

Step 5. Synthesis of a single-stranded oligonucleotide that contains encodes a flexible ten-amino acid linker and multiple cloning sites including Bgl II, Cla I, EcoR I, Sma I, BamH I, Nsi I and Spe I.

Step 6. Synthesis of a double-stranded oligonucleotide from the single-stranded oligonucleotide with DNA polymerase.

Step 7. Restriction of the double-stranded oligonucleotide with Bgl II and Spe I.

Step 8. Ligation of the double-stranded oligonucleotide into the compatible BamH I and Spe I sites in the vectors, which have first been restricted with BamH I and SpeI. The BamH I site in the Sp1 fragment is destroyed by the ligation.

Figure 2A:
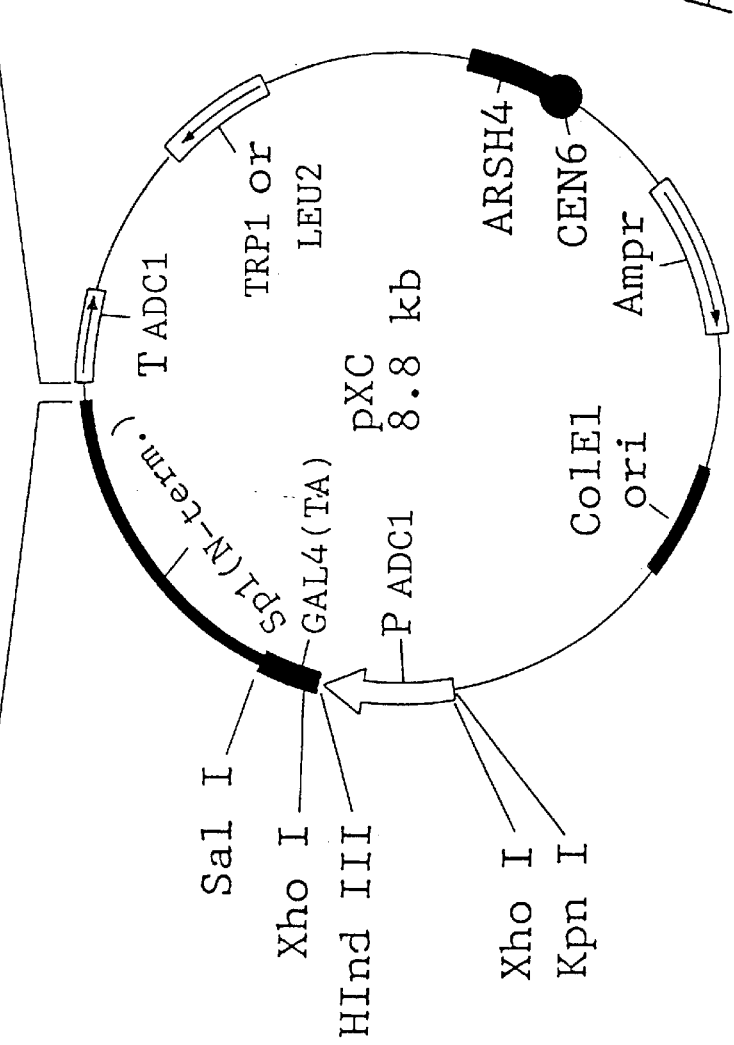
FIGS. 2A–C illustrate the construction of the yeast combinatorial libraries.

The resulting vector was named pXC, and the map is shown in FIG. 2A. The vectors for yeast combinatorial libraries and control vectors have been constructed based on this vector.

Figure 2B:
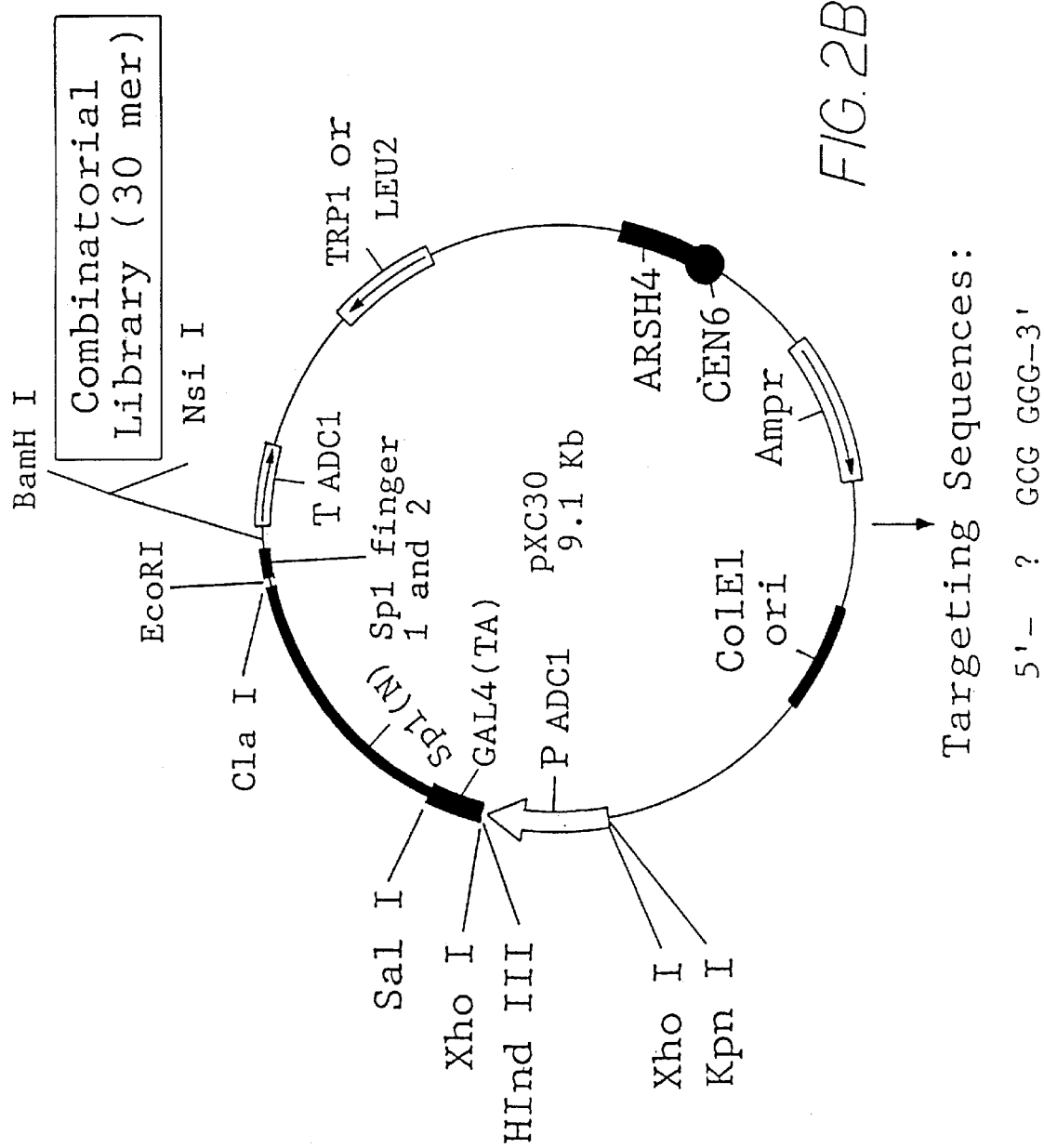
Figure 2C:
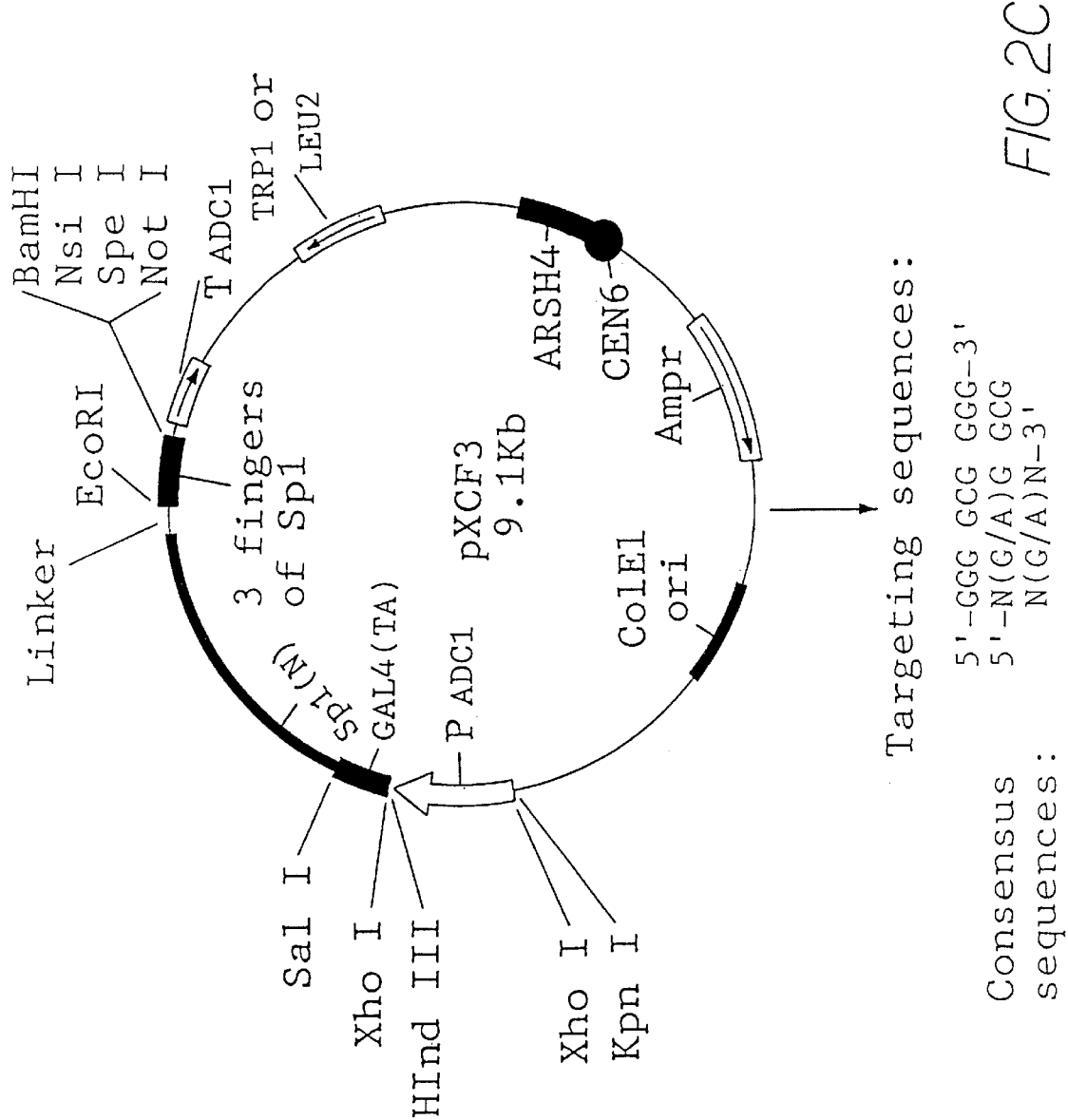

The vector for constructing yeast libraries was named pXCLF2. This vector was synthesized by putting a partial DNA binding domain (two zinc fingers) from Sp1 into pXC at EcoR I and BamH I sites (FIG. 2B). The yeast combinatorial library was then constructed by inserting random peptide libraries downstream from the two zinc fingers. The yeast combinatorial library peptides will target any DNA sequences close to the zinc finger binding sequences. A positive control vector (pXCLF3) was constructed by putting the three zinc finger region of Sp1 into the pXC vector at the same site (FIG. 2C). This vector will target wild-type Sp1 DNA binding sites.

EXAMPLE 3

Construction of the Yeast Combinatorial Library-pXC30

The general procedures used for constructing the yeast combinatorial library-pXC30 are as follows:

Step 1. Synthesis of 100-base single-stranded degenerate oligonucleotides.
Step 2. Synthesize double-stranded degenerate oligonucleotides from the single-stranded degenerate oligonucleotides using DNA polymerase.
Step 3. Purification of the double-stranded degenerate oligonucleotides.
Step 4. Restriction of the double-stranded degenerate oligonucleotides and purification of the restricted oligonucleotides.
Step 5. Ligation of the restricted oligonucleotides into vector pXCLF2.
Step 6. Generation of the yeast combinatorial library-pSC30 by electroporation.
Step 7. Harvesting the yeast combinatorial library.

EXAMPLE 4

Choosing the Targets and Establishing the Yeast Strains

The target DNA binding site sequences included:

| | | |
|---|---|---|
| (1) | Wild-type Sp1 binding sites (SEQ ID NO:1) | GAG GCG TGGC |
| (2) | Mutant Sp1 binding sites (SEQ ID NO:2) | AAA GCG TGGC |
| (3) | HIV Sp1 junction sites (SEQ ID NO:3) | TTTCCAGG GAG GCG |
| (4) | MDR Sp1 junction sites (SEQ ID NO:4) | CGCC GGG GCG |

The procedures for establishing the yeast strains can briefly be described as follows:

Step 1. Synthesis of single-stranded oligonucleotides containing two or four tandem repeats of the target sites.
Step 2. Making double-stranded oligonucleotides and purifying the oligonucleotides.
Step 3. Restricting the oligonucleotides with the appropriate restriction enzymes, and ligating the restricted oligonucleotides into three shuttle vectors: pRS315HIS, pHR307a, and p607Z. The vectors pRS315HIS and pHR307a contain a GAL1 minimum promoter and LEU2 or TRP1 marker genes, respectively. The vector p607Z contains a CYC1 minimum promoter and URA3 marker gene.
Step 4. Isolating the vector DNAs and verifying the sequences by sequencing.
Step 5. Transforming several yeast strains with the desired vector DNAs and growing the yeast in selective media.
Step 6. Examining the established yeast strains for background growth and selecting the best strains for further screening.

EXAMPLE 5

Testing the Specificity of the Three Zinc Finger Positive Control Vector

The positive control vector (pXCLF3) containing three zinc fingers was constructed and used to transform the yeast strains carrying different target sites. Two strains, yWAMZ and yM4271, previously found to display very low background growth, were used to establish target strains containing two or four wild-type or truncated Sp1 binding sites.

| | |
|---|---|
| wild-type Sp1 binding site (SEQ ID NO: 1) | GAG GCG TGGC |
| truncated Sp1 binding site (SEQ ID NO: 3) | TTTCCAGG GAG GCG |

The target strains were transformed with pXC3 (no zinc fingers) or pXCLF3 (three zinc fingers) and grown in (−) histidine or (+) X-gal plates. The three zinc finger-containing vector specifically turned on HIS3 and LacZ genes only in strains containing the wild-type Sp1 binding sites, but not in those strains containing the mutated Sp1 binding sites (data not shown).

EXAMPLE 6

Testing the Activity of Individual Zinc Fingers of Sp1

The DNA binding activities of the individual zinc fingers of Sp1 were assessed. All three zinc fingers were required to specifically recognize the wild-type Sp1 binding sites and to turn on HIS3 or LacZ gene expression in the various yeast strains tested. The pXCLF2 vector, which contains only two Sp1 zinc fingers, failed to induce either HIS3 or LacZ gene expression (data not shown).

EXAMPLE 7

Testing the Size of the "Screening Window"

A "screening window" was established by testing the growth-promoting effects of the three zinc finger construct (positive control) and the two zinc finger construct (negative control) in the presence of various concentrations of the drug 3'-AT, a competitive inhibitor of histidine. There is at least a 100-fold difference in sensitivity to 3'-AT between the positive and negative controls (data not shown). These results indicate that we could suppress background growth and identify relatively weakly-binding novel peptides in the library at low 3'-AT concentrations and pick out stronger binders at high 3'-AT concentrations.

EXAMPLE 8

Screening the Yeast Combinatorial Library

An initial library screen was done in the absence of 3'-AT. A histidine-requiring yeast strain containing four Sp1 binding sites upstream of the HIS3 gene was transformed with the yeast combinatorial library DNA, and the transfectants were grown in (−) histidine plates. A number of colonies growing on (−) histidine plates were clonally isolated and then tested for their ability to grow in the presence of increasing concentrations of 3'-AT. Some of these clones grew as well as the positive control did under the same conditions. Plasmids were isolated from these clones and used to transform a yeast strain containing the LacZ gene downstream from four Sp1 binding sites. Two LacZ positive clones were detected. The plasmids from these clones were isolated and sequenced. Peptide sequences identified in this manner are listed in FIG. 4.

EXAMPLE 9

Peptides that Exhibit Sequence Specific Binding to Wild-Type Sp1 Sites

Peptide A46-2

The process described in the Example 8 was carried out to identify peptides showing sequence-specific binding to wild-type Sp1 binding site DNA (SEQ ID NO:1). The presumptive sequence of the library insert region in clone A46-2 is:
QGAISNGTGD AGPGWLKRPP FWNPERPNNK (SEQ ID NO:5)

Although this peptide binds effectively to Sp1 sites, it does not resemble a zinc finger, nor does it have an obvious resemblance to other sequences identified by practice of the present invention, nor any sequences in the protein data banks.

EXAMPLE 10

Peptides that Exhibit Sequence Specific Binding to Wild-Type Sp1 Sites

Peptide G1-2

The process described in the Example 8 was carried out to identify peptides showing sequence-specific binding to wild-type Sp1 binding site DNA (SEQ ID NO:1). The presumptive sequence of the library insert region in clone G1-2 is:
WQRMRVWDEC GIMGSDHPLE LNECPGEYTV (SEQ ID NO:6)

Although this peptide binds effectively to Sp1 sites, it does not resemble a zinc finger, nor does it have an obvious resemblance to other sequences identified by practice of the present invention, nor any sequences in the protein data banks.

EXAMPLE 11

Peptides that Exhibit Sequence Specific Binding to Wild-Type Sp1 Sites

Peptide G12-1

The process described in the Example 8 was carried out to identify peptides showing sequence-specific binding to wild-type Sp1 binding site DNA (SEQ ID NO:1). The presumptive sequence of the library insert region in clone G12-1 is:
AESKLMRGVI LPLKSILYRL RFRLRCYRLW (SEQ ID NO:7)

Although this peptide binds effectively to Sp1 sites, it does not resemble a zinc finger, nor does it have an obvious resemblance to other sequences identified by practice of the present invention, nor any sequences in the protein data banks.

EXAMPLE 12

Peptides that Exhibit Sequence Specific Binding to Wild-Type Sp1 Sites

Peptide H3-2

The process described in the Example 8 was carried out to identify peptides showing sequence-specific binding to wild-type Sp1 binding site DNA (SEQ ID NO:1). The presumptive sequence of the library insert region in clone H3-2 is:
NDRVFGDYSY FGGACAFVLA FGSVCCGELC (SEQ ID NO:8)

Although this peptide binds effectively to Sp1 sites, it does not resemble a zinc finger, nor does it have an obvious resemblance to other sequences identified by practice of the present invention, nor any sequences in the protein data banks.

EXAMPLE 13

Peptides that Exhibit Sequence Specific Binding to Wild-Type Sp1 Sites

Peptide H9-1

The process described in the Example 8 was carried out to identify peptides showing sequence-specific binding to wild-type Sp1 binding site DNA (SEQ ID NO:1). The presumptive sequence of the library insert region in clone H9-1 is:
WPVRRRNRNC CVWDGGYWDF CGADCDAVCV (SEQ ID NO:9)

This high cysteine content of this peptide suggests some resemblance to a zinc finger. This peptide does not have an obvious resemblance to other sequences identified by practice of the present invention, nor any sequences in the protein data banks.

EXAMPLE 14

Peptides that Exhibit Sequence Specific Binding to Wild-Type Sp1 Sites

Peptide H13-4

The process described in the Example 8 was carried out to identify peptides showing sequence-specific binding to wild-type Sp1 binding site DNA (SEQ ID NO:1). The presumptive sequence of the library insert region in clone H13-4 is:
NVSVVCAVVW FSCSLVSYAS GVYGGGSDSG (SEQ ID NO:10)

Although this peptide binds effectively to Sp1 sites, it does not resemble a zinc finger, nor does it have an obvious resemblance to other sequences identified by practice of the present invention, nor any sequences in the protein data banks.

EXAMPLE 15

Peptides that Exhibit Sequence Specific Binding to Wild-Type Sp1 Sites

Peptide K20-1

The process described in the Example 8 was carried out to identify peptides showing sequence-specific binding to wild-type Sp1 binding site DNA (SEQ ID NO:1). The presumptive sequence of the library insert region in clone K20-1 is:
MRRLIYGHAP LQNNALSCRQ GAGPKGAERL (SEQ ID NO:11)

Although this peptide binds effectively to Sp1 sites, it does not resemble a zinc finger, nor does it have an obvious resemblance to other sequences identified by practice of the present invention, nor any sequences in the protein data banks.

EXAMPLE 16

Peptides that Exhibit Sequence Specific Binding to Wild-Type Sp1 Sites

Peptide K38-2B

The process described in the Example 8 was carried out to identify peptides showing sequence-specific binding to wild-type Sp1 binding site DNA (SEQ ID NO:1). The presumptive sequence of the library insert region in clone K38-2B is:

EVWLYRGPLL WSIAKKAFYA VLMGMVVLVL (SEQ ID NO:12)

Although this peptide binds effectively to Sp1 sites, it does not resemble a zinc finger, nor does it have an obvious resemblance to other sequences identified by practice of the present invention, nor any sequences in the protein data banks.

EXAMPLE 17

Peptides that Exhibit Sequence Specific Binding to Mutant Sp1 Sites

Peptide G4-4

The process described in the Example 8 was carried out to identify peptides showing sequence-specific binding to mutant Sp1 binding site DNA (SEQ ID NO:2). The presumptive sequence of the library insert region in clone G4-4 is:
VFRPLTFEST FFNSGLLFQT GTTLNPISVY (SEQ ID NO:13)

Although this peptide binds effectively to Sp1 sites, it does not resemble a zinc finger, nor does it have an obvious resemblance to other sequences identified by practice of the present invention, nor any sequences in the protein data banks.

EXAMPLE 18

Peptides that Exhibit Non-Specific DNA Binding

Peptide A97-3 and H18-1

The process described in the Example 8 was carried out to identify peptides showing sequence-specific binding to wild-type (SEQ ID NO:1) and mutant (SEQ ID NO:2) SP1 binding site DNA. In two different rounds of screening, a clone was isolated expressing a peptide that exhibited non-specific DNA binding. The sequences in the two clones were identical. The presumptive sequence of the library insert region in clones A97-3 and H18-1 are:
RRCAGLASRV TSRSLGELEG ANSLRKYFRR (SEQ ID NO:14)

Although this peptide binds effectively to Sp1 sites, it does not resemble a zinc finger, nor does it have an obvious resemblance to other sequences identified by practice of the present invention, nor any sequences in the protein data banks.

EXAMPLE 19

Screening for Non-Toxic Drugs That Block Specific Transcriptional Events

The basic process described in the previous examples can be modified to screen for low molecular weight compounds that either (a) bind to a specific DNA sequence, or (b) interfere with a specific transcription factor that binds to a DNA sequence.

Yeast are transfected with a vector expressing a mammalian transcription factor and co-transfected with a vector containing the DNA binding site for this transcription factor located upstream of the gene for herpes virus thymidine kinase (TK). The viral TK is expressed, and under normal conditions will not be detrimental to the host cell. When the anti-viral nucleoside drug ganciclovir is added to the culture, the viral TK phosphorylates and activates the ganciclovir to form a toxic intermediate, which inhibits DNA synthesis and eventually induces death of the host cell.

Figure 3:
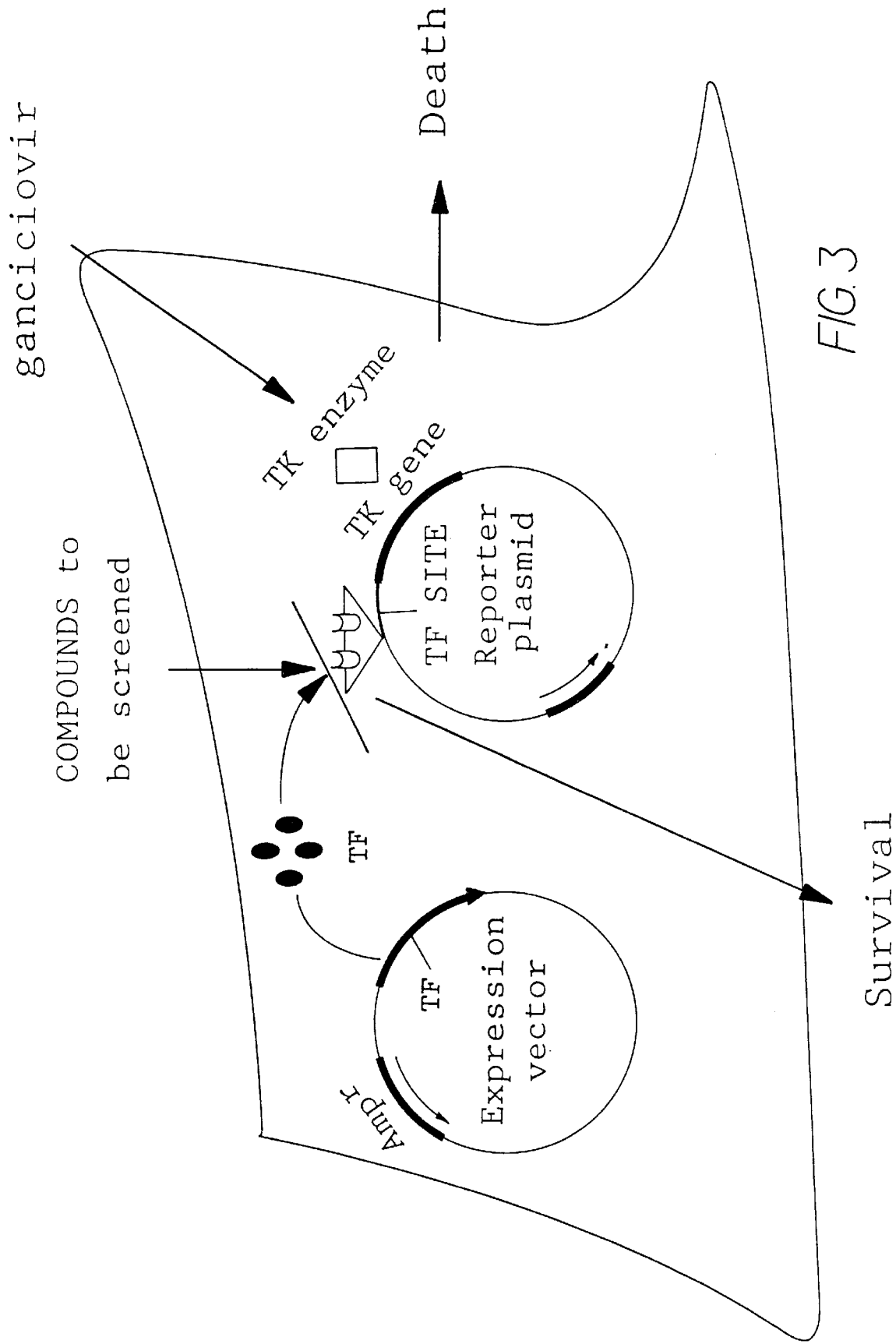
FIG. 3 shows an in vivo system employing the present invention for screening compounds that specifically interfere with a transcription factor or its DNA binding site. TF=transcription factor; TK=thymidine kinase.

This system can be used to screen for compounds that selectively block a specific transcriptional event—activation of TK by the plasmid-encoded transcription factor introduced into the host cell. The screening process is based on the principle that if a compound is added to the culture, and this compound blocks expression of the viral TK, then the toxic effects of ganciclovir are prevented and host cells survive. The use of this strategy for drug screening is illustrated in FIG. 3. The compounds to be screened can simply be added to the medium in which the host cells are cultured, or they can be expressed by a co-transfected combinatorial library.

This strategy has several important features: First, it is easily adapted to a 96-well format and is thus suitable for rapid screening by robotics. Second, the rapid growth of yeast cells contributes to ease and rapidity of screening. Last, since this system uses a positive selection for growth, drug candidates that are themselves highly cytotoxic are automatically excluded.

The foregoing examples are illustrative of the present invention, and are not to be construed as limiting thereof. The invention is defined by the following claims, with equivalents of the claims to be included therein.

---

That which is claimed is:

1. A method for identifying sequence-specific DNA-binding peptides, comprising the steps of:
   (a) providing host cells containing selectable markers;
   (b) providing a recombinant vector containing a coding sequence encoding a protein that controls gene transcription when in proximity to a target DNA sequence, said target DNA sequence comprising a regulatory element, and said recombinant vector containing a selectable marker;
   (c) inserting into said coding sequence in a plurality of said recombinant vectors a random oligonucleotide so that the resulting vectors encode a plurality of different fusion proteins, each containing said protein of step (b) and a peptide encoded by said random oligonucleotide;
   (d) providing a reporter vector, said reporter vector comprising a reporter gene operably associated with said DNA regulatory element of step (b) and a selectable marker;
   (e) co-transfecting said host cells with said DNA vectors of step (c) and said reporter vectors; and
   (f) culturing said transfected host cells in a selective medium, so that only those host cells containing a vector DNA of step (c) expressing a fusion protein that contains a peptide capable of sequence-specific binding to said target DNA sequence of step (d) grow therein; and
   (g) selecting at least one host cell from step (f) that expresses said reporter gene of step (d); and then
   (h) isolating the peptide encoded by said random oligonucleotide of step (c) from said at least one host cell of step (g), where said peptide exhibits sequence-specific binding to said target DNA of step (b).

2. A method according to claim 1, wherein said DNA regulatory element is a promoter sequence of a gene.

3. A method according to claim 2, wherein said reporter vector contains a minimal promoter, said promoter sequence located 5' to said minimal promoter.

4. A method according to claim 1, wherein said reporter vector is a plasmid.

5. A method according to claim 1, wherein said host cells are yeast cells.

6. A method according to claim 5, wherein said host cells are deficient in HIS3, LEU2 and TRP1, wherein said selectable marker in said vector DNA is TRP1, wherein said reporter gene is HIS3, and wherein said selectable marker in said reporter plasmid is LEU2.

7. A method according to claim 5, wherein said protein of step (b) is the transactivating domain of Gal4.

8. A method according to claim 1, wherein said peptide capable of binding to said target DNA sequence is not more than 60 amino acid residues in length.

9. A method according to claim 1, wherein said peptide capable of binding to said target DNA sequence is not more than 30 amino acid residues in length.

10. A method according to claim 1, wherein said peptide capable of binding to said target DNA sequence is not more than 10 amino acid residues in length.

11. A method according to claim 1, wherein at least 1 nucleotide of said target DNA sequence is no more than 1000 nucleotides away from a transcription start site of said gene.

12. A method according to claim 1, wherein at least 1 nucleotide of said target DNA sequence is no more than 200 nucleotides away from a transcription start site of said gene.

13. A method according to claim 5, wherein said reporter gene is selected from the group consisting of URA3, HIS3, LEU2 and TRP1 genes.

14. A method according to claim 1, wherein said coding sequence of step (b) includes a nucleotide sequence encoding a truncated DNA binding protein, said truncated DNA binding protein exhibiting no significant DNA binding to said regulatory element of step (b).

15. A method according to claim 14, wherein said nucleotide sequence encoding said truncated DNA binding protein is positioned 5' to said random oligonucleotide of step (c).

16. A method according to claim 14, wherein said truncated DNA binding protein is a zinc finger protein.

17. A method according to claim 16, wherein said truncated DNA binding protein is Sp1.

18. A method for identifying sequence-specific DNA-binding peptides, comprising the steps of:
    (a) providing host cells containing selectable markers;
    (b) providing a recombinant vector containing a coding sequence encoding a protein that controls gene transcription when in proximity to a target DNA sequence, said target DNA sequence comprising a regulatory element, and said recombinant vector containing a selectable marker;
    (c) inserting into said coding sequence in a plurality of said recombinant vectors a random oligonucleotide so that the resulting vectors encode a plurality of different fusion proteins, each containing said protein of step (b) and a peptide encoded by said random oligonucleotide;
    (d) providing a reporter vector, said reporter vector comprising a reporter gene operably associated with said DNA regulatory element of step (b) and a selectable marker;
    (e) co-transfecting said host cells with said DNA vectors of step (c) and said reporter vectors; and
    (f) culturing said transfected host cells in a selective medium, so that those host cells containing a vector DNA of step (c) expressing a fusion protein that contains a peptide capable of sequence-specific binding to said target DNA sequence of step (d) can be identified; and
    (g) selecting at least one host cell from step (f) that expresses said reporter gene of step (d); and then
    (h) isolating the peptide encoded by said random oligonucleotide of step (c) from said at least one host cell of step (g), where said peptide exhibits sequence-specific binding to said target DNA of step (b).

19. A method according to claim 18, wherein said reporter gene is the LacZ gene.

20. A method according to claim 18, wherein said DNA regulatory element is a promoter sequence of a gene.

21. A method according to claim 20, wherein said reporter vector contains a minimal promoter, said promoter sequence located 5' to said minimal promoter.

22. A method according to claim 18, wherein said reporter vector is a plasmid.

23. A method according to claim 18, wherein said host cells are yeast cells.

24. A method according to claim 23, wherein said protein of step (b) is the transactivating domain of Gal4.

25. A method according to claim 18, wherein said peptide capable of binding to said target DNA sequence is not more than 60 amino acid residues in length.

26. A method according to claim 18, wherein said peptide capable of binding to said target DNA sequence is not more than 30 amino acid residues in length.

27. A method according to claim 18, wherein said peptide capable of binding to said target DNA sequence is not more than 10 amino acid residues in length.

28. A method according to claim 18, wherein at least 1 nucleotide of said target DNA sequence is no more than 1000 nucleotides away from a transcription start site of said gene.

29. A method according to claim 18, wherein at least 1 nucleotide of said target DNA sequence is no more than 200 nucleotides away from a transcriptions tart site of said gene.

30. A method according to claim 18, wherein said coding sequence of step (b) includes a nucleotide sequence encoding a truncated DNA binding protein, said truncated DNA binding protein exhibiting no significant DNA binding to said regulatory element of step (b).

31. A method according to claim 30, wherein said nucleotide sequence encoding said truncated DNA binding protein is positioned 5' to said random oligonucleotide of step (c).

32. A method according to claim 30, wherein said truncated DNA binding protein is a zinc finger protein.

33. A method according to claim 32, wherein said truncated DNA binding protein is Sp1.

\* \* \* \* \*

UNITED STATES PATENT AND TRADEMARK OFFICE
CERTIFICATE OF CORRECTION

PATENT NO. : 5,869,250  Page 1 of 2
DATED : February 9, 1999
INVENTOR(S) : Xiaojun Cheng, et al It is certified that error appears in the above-indentified patent and that said Letters Patent is hereby corrected as shown below:

On the title page, item

[56] Publications,    "C. Inouye et al., "Isolation of a cDNA Encoding a Metal Response Elelment Binding Protein Using a Novel Expression Cloning Procedure: The One Hybrid System", DNA Cell Biol. 13(7): 731-742, Jul. 1994." should read -- C. Inouye et al., "Isolation of a cDNA Encoding a Metal Response Element Binding Protein Using a Novel Expression Cloning Procedure: The One Hybrid System", DNA Cell Biol. 13(7): 731-742, Jul. 1994.

[56]    The following documents should be added:

References Cited

U.S. PATENT DOCUMENTS 5,270,163  12/14/93  Gold et al. ...............................435/6
5,270,170  12/14/93  Schatz et al. .........................35/7.37
5,283,173   2/1/94   Fields et al. ............................435/6
5,468,614  11/21/95  Fields et al. ............................435/6
5,498,530   3/12/96  Schatz, et al. ......................435/69.1
5,498,538   3/12/96  Kay et al. ...........................435/69.1

FOREIGN PATENT DOCUMENTS

WO86/00991 of 2/13/86 WIPO
WO93/20242 of 10/14/93 WIPO
WO92/14842 of 9/3/92 WIPO
WO92/14843 of 9/3/92 WIPO
WO96/06166 of 2/29/96 WIPO

UNITED STATES PATENT AND TRADEMARK OFFICE
CERTIFICATE OF CORRECTION

PATENT NO. : 5,869,250
DATED : February 9, 1999
INVENTOR(S) : Xiaojun Cheng, et al It is certified that error appears in the above-indentified patent and that said Letters Patent is hereby corrected as shown below:

PUBLICATIONS

Sedlak, "Roche Researchers Devise a Yeast Tribrid System For the Process of Drug Discovery", Genetic Engineering News, May 1, 1996.

Choo, et al., "In Vivo Repression by a Site-Specific DNA-Binding Protein Designed Against an Oncogenic Sequence", Nature, Vol. 372, December 15, 1994.

Rebar et al., "Zinc Finger Phage: Affinity Selection of Fingers With New DNA-Binding Specificities", Science, Vol. 263, February 4, 1994.

Baum, "Combinatorial Approaches Provide Fresh Leads for Medicinal Chemistry", Science/Technology, February 7, 1994.

Signed and Sealed this

Twelfth Day of October, 1999

Attest:

Q. TODD DICKINSON

Attesting Officer

Acting Commissioner of Patents and Trademarks